US006491893B1

(12) United States Patent
Babich

(10) Patent No.: US 6,491,893 B1
(45) Date of Patent: Dec. 10, 2002

(54) COMPOUNDS FOR TARGETING AND IMAGING INFECTION AND INFLAMMATION

(75) Inventor: John W. Babich, Scituate, MA (US)

(73) Assignee: Biostream, Inc., Cambridge, MA (US)

( * ) Notice: Subject to any disclaimer, the term of this patent is extended or adjusted under 35 U.S.C. 154(b) by 0 days.

(21) Appl. No.: 09/553,006

(22) Filed: Apr. 20, 2000

Related U.S. Application Data

(63) Continuation-in-part of application No. PCT/US00/01289, filed on Jan. 19, 2001.
(60) Provisional application No. 60/116,364, filed on Jan. 19, 1999.

(51) Int. Cl.$^7$ .......................... A61K 51/00; Q61B 5/055
(52) U.S. Cl. .................... 424/1.41; 424/1.69; 424/9.34; 424/1.85; 424/1.89
(58) Field of Search .............................. 424/1.69, 1.41, 424/1.85, 1.89, 9.3, 9.34, 9.36, 9.4, 9.5, 9.6, 9.1; 534/10, 14

(56) References Cited

U.S. PATENT DOCUMENTS

| | | | |
|---|---|---|---|
| 4,810,643 A | 3/1989 | Souza | 435/68 |
| 4,999,291 A | 3/1991 | Souza | 435/69.1 |
| 5,032,676 A | 7/1991 | Deeley et al. | 530/351 |
| 5,108,899 A * | 4/1992 | Allen | 435/7.21 |
| 5,214,132 A | 5/1993 | Kuga et al. | 530/351 |
| 5,218,092 A | 6/1993 | Sasaki et al. | 530/351 |
| 5,229,496 A | 7/1993 | Deeley et al. | 530/351 |
| 5,580,755 A | 12/1996 | Souza | 435/69.5 |
| 5,670,133 A | 9/1997 | Zamora | |
| 5,676,941 A | 10/1997 | Souza | 424/85.1 |

FOREIGN PATENT DOCUMENTS

| | | |
|---|---|---|
| WO | WO 95/11045 | 4/1995 |
| WO | WO 96/15816 | 5/1996 |

OTHER PUBLICATIONS

Burguess et al.; "Granulocyte/macrophage Colony–Stimulating Factor from Mouse Lung Conditioned Medium", Biochem. J. 235: 805–814, (1986).

Cebon et al.; "Pharmacokinetics of Human Granulocyte–Macrophage Colony–Stimulating Factor Using A Sensitive Immunoassay", Blood, 72(4): 1340–1347 (Oct. 1988).

Eguchi et al.; "Dose Escalation Study of Recombinant Human Granulocyte–Colony–Stimulating Factor (KRN8601) in Patients with Advanced Malignancy", Cancer Reseach 49: 5221–5224 (Sep. 15, 1989).

Gough et al.; "Mutagenesis of Murine Granulocyte/Macrophage–Colony–Stimulating Factor Reveals Critical Residue Near the N Terminus", Euro. J. Biochem. 169: 353–358 (1987).

Sparrow et al.; "Purification and Partial Amino Acid Sequence of Asialo Murine Granulocyte–Macrophage Colony Stimulating Factor", Proc. Natl. Acad. Sci. USA, 82: 292–296 (Jan. 1985).

Thakur et al.; "Monoclonal Antibodies as Agents for Selective Radiolabeling of Human Neutrophils", J. Nucl. Med. 29(11): 1817–1825 (Nov. 1988).

International Search Report for PCT/US00/01289, dated Aug. 17, 2000.

Ralph, L.D. et al., "Site–Specific Conjugation of Diethylenetriaminepentaacetic Acid to Recombinant Human Granulocyte–Colony–Stimulating Factor: Preservation of Protein Structure and Function", Biochem. vol. 34, pp. 4889–4897, 1995, XP–002087163.

Broudy, V.C. et al., "Monoclonal Antibody 4B10 (M33) Recognizes Stem Cell Factor (SCF), and Antibody VIMD2b (M16) Recognizes the Receptor for Granulocyte Colony Stimulating Factor (G–CSF)", Tissue Antigens, vol. 42(4), p. 331, 1993, Abstract CR013, XP–002122101.

Fischmann, A.J. et al., "Imaging Focal Sites of Bacterial Infection in Rats with Indium–111–Labeled Chemotactic Peptide Analogs", J. of Nuc. Med., vol. 32(3), pp. 483–491, 1991, XP–002127484.

Connors, J.M. et al., "Pharmacokinetics and Biodistribution of In–111–DPTA–G–CSF in Non–Human Primates", J. of Nuc. Med., vol. 39(5), Abstract No. 843, 1998, XP–002144005.

Connors, J.M. et al., "Human Pharmacokinetics and Biodistribution of In–111–DPTA–G–CSF", J. of Nuc. Med., vol. 40(5), Abstract No. 1031, 1999, XP–002144006.

* cited by examiner

Primary Examiner—Michael G. Hartley
(74) Attorney, Agent, or Firm—Foley Hoag LLP

(57) ABSTRACT

The present invention provides novel agents for specifically targeting and detecting or treating focal sites of infection or inflammation in a subject.

27 Claims, 1 Drawing Sheet

COMPOUNDS FOR TARGETING AND IMAGING INFECTION AND INFLAMMATION

This Application is a continuation-in-part of PCT/US00/01289, filed Jan. 19, 2001, which claims the benefit of U.S. Serial No. 60/116,364, filed Jan. 19, 1999, the contents of which are incorporated herein by reference in their entireties.

BACKGROUND OF THE INVENTION

Gallium-67 ($^{67}$Ga), which binds in vivo to the plasma protein transferring, was the first true radionuclide infection imaging agent and still is the primary radiopharmaceutical used to detect infection. However, the target-to-background ratio of this agent is relatively low compared to more recently developed agents. In addition, normal physiological accumulation of gallium in the liver, spleen, gastrointestinal tract, and kidneys makes evaluation of the abdomen difficult. There is also significant bone uptake, which can make it difficult to diagnose osteomyelitis. Gallium scans frequently require 24 to 72 hours or more of delayed imaging to make a definite diagnosis. Further, $^{67}$Ga shows uptake in a significant number of tumors, making it less useful in detecting infection in cancer patients and less specific for injection in general.

Although exhibiting higher specificity, $^{111}$In and $^{99m}$Tc labeled leukocytes (granulocytes) are relatively difficult to prepare since, to avoid an immune response, the subject's own neutrophils must be harvested and labeled in vitro, prior to in vivo administration. In addition, relatively high levels of this agent has been found to accumulate in the liver, spleen and bone marrow.

Monoclonal antibodies, both whole and Fab' fragments, have also been developed. Examples include: $^{123}$I-anti-nonspecific cross-reacting antigen (NCA)-95 immunoglobulin (Ig) G1 antibody (NCA) (Locher JTh et al., (1986) Nucl. Med Comm 7:659–670), a $^{99m}$Tc-anti-NCA-90 Fab' fragment (Becker, W et al., (1992) J. Nucl. Med 33: 1817–1825), and $^{99m}$Tc-anti-stage-specific embryonic antigen-1 (SSEA-1) IgM antibody (Thakur, M L (1988) J. Nucl. Med. 29: 1817–1825). High contrast imaging can be achieved by allowing a nonradiolabeled antibody to localize and clear from the circulation prior to administration of a low molecular weight, radiolabeled moiety with high affinity for the pretargeted moiety. One such method utilizes the high affinity of avidin, a cationic glycoprotein found in egg whites, for biotin, a naturally occurring vitamin. Avidin (or streptavidin) is capable of binding four biotin molecules and forming an avidin-biotin complex with a very high affinity. (Kd=$10^{-15}$M). However, this pretargeting, "two-step" approach, requires that a subject be available to undergo multiple procedures over the course of a few days.

Despite the success of several agents for imaging infection, at least 24 hours is typically required before lesions can be visualized. From a clinical perspective, this is a serious deficiency. Safe and effective agents that rapidly localize at a site of infection or inflammation and produce a clear image are needed.

SUMMARY OF THE INVENTION

In one aspect, the invention features agents comprised of a colony stimulating factor (CSF), which specifically target sites of infection or inflammation in a subject in vivo. Preferred CSFs are selected from the group consisting of: granulocyte colony-stimulating factor (G-CSF), granulocyte-macrophage colony-stimulating factor (GM-CSF), monocyte colony stimulating factor (M-CSF or CSF-1) and binding fragments thereof. For use in the invention, a CSF may be: i) purified or recombinant; ii) wildtype (natural) or a variant (mutant); iii) fully, partially or non-glycosylated; iv) a full-length protein, polypeptide or peptide; or v) human or non-human. Particularly preferred agents show a target to non-target ratio of at least about 5:1, are stable in vivo and substantially localize to target within about 18 hours after administration, more preferably within about 10 or 8 hours and optimally within about 4 hours after administration.

In one embodiment, the agent is a pharmaceutical composition comprised of a CSF and a therapeutic agent. Preferred therapeutic agents are capable of preventing the establishment of or treating a site of infection or inflammation. Examples include antimicrobial agents and antiinflammatory agents including non-steroidal and steroidal compounds. In another embodiment, the agent is an imaging agent comprised of a CSF and a label. Preferred labels are radionuclides. Particularly preferred radionuclides are selected from the group consisting of radioisotopes with physical decay characteristics ideal for γ-camera and/or PET camera imaging $^{123}$I, $^{99m}$Tc, $^{18}$F, $^{68}$Ga, $^{62}$Cu, $^{64}$Cu, $^{55}$Co, $^{111}$In. The invention further features kits for use in treating or imaging a site of infection or inflammation in a subject.

In another aspect, the invention features methods for preventing or treating a site of infection or inflammation in a subject, comprising administering to the subject a therapeutically effective amount of a pharmaceutical composition comprising a colony stimulating factor and a therapeutic agent.

In a further aspect, the invention features methods for imaging a site of infection or inflammation in a subject, comprising administering to the subject a diagnostically effective amount of a composition comprising a colony stimulating factor and a therapeutic agent.

The diagnostic agents of the invention rapidly localize at sites of infection or inflammation. In addition, the agents exhibit a relatively high target-to-background ratio and rapid clearance from the background and the target, particularly when administered as a bolus intravenously. Further, clinical pharmacokinetic studies indicate that administration of colony stimulating factors in an amount effective for targeting would be relatively safe.

Other features and advantages of the invention will be apparent from the following detailed description and claims.

DETAILED DESCRIPTION OF THE INVENTION

Definitions

Figure 1:
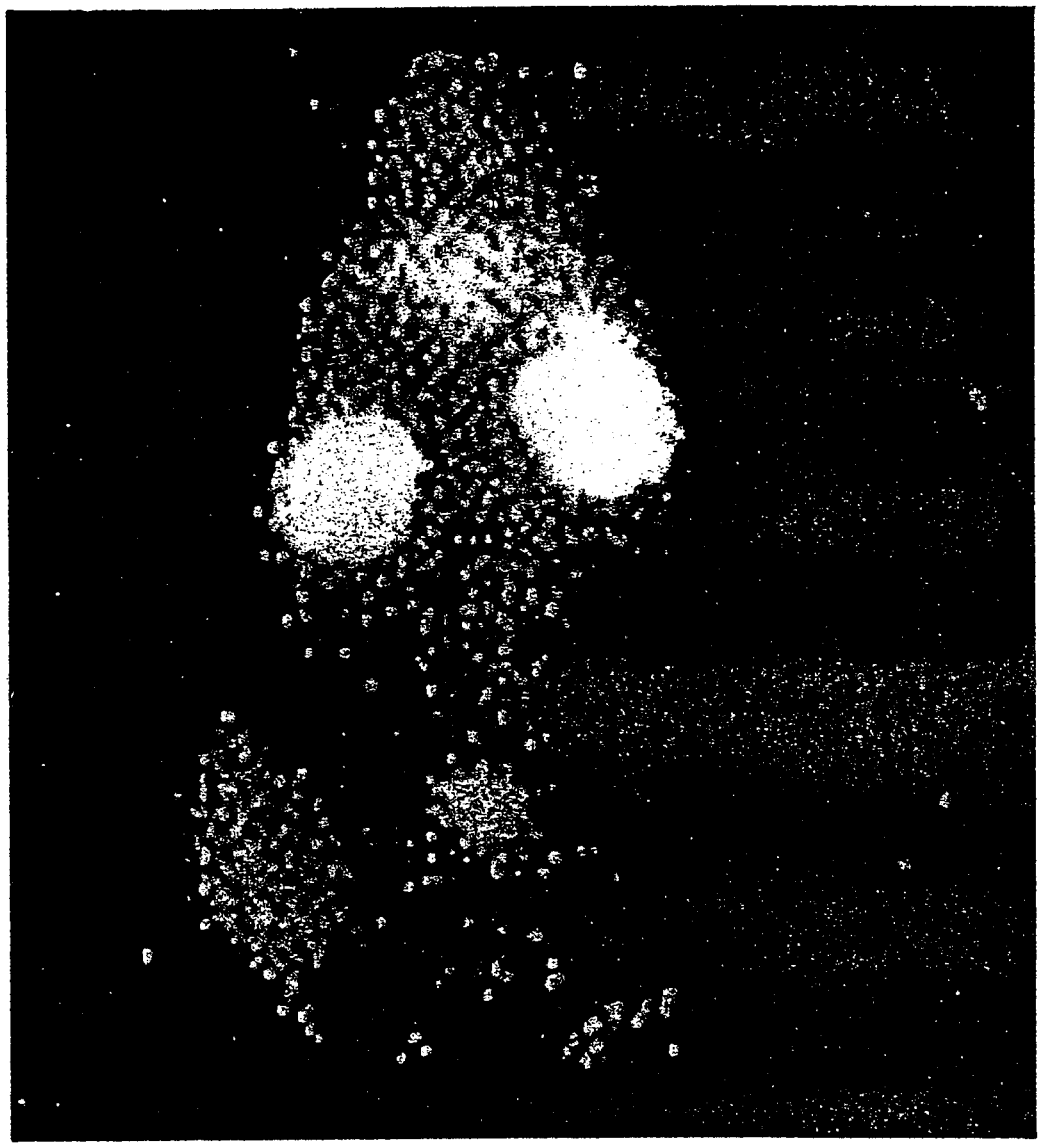
FIG. 1 shows a gamma camera image (anterior) of a rabbit at 18 hr after injection of In-111-DTPA-G-CSF.

For convenience, the meaning of certain terms and phrases employed in the specification, examples, and appended claims are provided below.

As used herein, a "Colony Stimulating Factor" or "CSF" refers to a molecule that is capable of binding to a hematopoietic stem cell or a cell of the myelomonocytic lineage that is differentiated from a hematopoietic stem cell. Examples of myelomonocytic cells differentiated from hematopoietic stem cells, include: colony-forming unit, granulocyte-erythrocyte-monocyte-megakaryocyte (CFU-GEMM), CFU megakaryocyte (CFU-MEG), CFU-eosinophil (CFU-EO), CFU-granulocyte/monocyte (CFU-GM), CFU-erythroid (CFU-E), monocytes and neutrophils. Examples of CSFs include: granulocyte colony-stimulating factor (G-CSF), granulocyte-macrophage colony-stimulating factor (GM-CSF), monocyte colony stimulating factor (M-CSF or CSF-1) and binding fragments thereof. For use in the invention, a CSF may be: i) purified or recombinant; ii) wildtype (natural) or a variant (mutant); iii) fully, partially or non-glycosylated; iv) a full-length protein or binding fragment; or v) human or non-human.

"Colony Stimulating Factor 1 (CSF-1, also known as M-CSF) is distinguished from other colony stimulating factors in its ability to stimulate the formation of predominantly macrophage colonies. A "short" form that encodes a monomeric protein of 224 amino acids preceded by a 32 amino acid signal sequence (Kawasaki et al., (1985) Science 230:292–296); and a "long" form encoding a monomeric protein of 522 amino acids, also preceded by the 32 amino acid signal sequence. The amino acid sequence of the short form is shown herein as SEQ. I.D. No. 1 and the amino acid sequence of the long form is shown herein as SEQ I.D. No. 2.

"Granulocyte colony stimulating factor" or "G-CSF" refers to a full length protein, polypeptide or peptide that substantially corresponds in sequence to a natural G-CSF or a fragment thereof and that binds to a CSF receptor. Two naturally occurring forms of G-CSF exist with 204 or 207 amino acids, of which the first 30 represent a signal. These two forms are a consequence of alternative splicing in the second intron. Both forms have five cysteine residues; four forming two disulfide bonds and one free. Binding studies have shown that G-CSF binds to G-CSF receptors on CFU-GM and neutrophils. None or only slight binding is observed with erythroid, lymphoid, eosinophilic cell lines as well as macrophages. The amino acid sequence of natural human G-CSF is presented herein as SEQ. ID. No. 1 (See also U.S. Pat. Nos. 4,810,643; 4,999,291; and 5,676,941). At least two kinds of rhG-CSF are available on the world market: Escherichia coli derived G-CSF (filgrastim), which has no sugar chain; and Chinese hamster ovary cell derived G-CSF (renograstrim), which has a sugar chain at Thr-133. The amino acid sequence of natural bovine G-CSF is presented herein as SEQ. ID. No. 2. In addition to these natural proteins, functional variants, that are easier to isolate from recombinant culture, have been developed, based on the replacement of one or more cysteine residue (e.g. at positions 17, 36, 42, 64 and/or 74) by a serine residue. (See e.g. U.S. Pat. No. 5,580,755). Additional variants of natural G-CSF, which contain an alanine at position 1, a threonine at position 3, a tyrosine at position 4, an arginine at position 5, a serine at position 17, an asparagine at position 145 or a serine at position 147 and that exhibit increased in vivo half-life have also been described (See e.g. U.S. Pat. Nos. 5,218,092 and 5,214,132). G-CSF has proven to be clinically effective in promoting recovery in patients with chemo- or radiotherapy-induced neutropenia. Both radioimmunoassay and bioassays have been used to measure the pharmacokinetics of G-CSF (Eguchi, K et al., (1989) Cancer Res. 49:5221–24). Peak serum concentrations have been reported to be proportional to dose, both for intravenous and subcutaneous routes. C sub max values are maintained for 30–60 min after short (20–30 min) intravenous infusions before concentrations decline logarithmically with time. The estimated terminal half-life for G-CSF after short intravenous infusions is 0.75–7.2 h for doses up to 60 m$\mu$ g/kg. After single subcutaneous injections, serum concentrations peak in 4–6 h, and by 24 h, serum concentrations are <10% C sub max. After doses of 5–10 m$\mu$ g/kg, serum concentrations of >10 ng/mL are maintained for up to 16 h.

"Granulocyte-Macrophage Colony Stimulating Factor" or "GM-CSF" is naturally produced by many cell types and has been found to promote growth of progenitors of several myeloid lines and, to a lesser extent, of the megakaryocyte line. Its main effects are to increase neutrophil and monocyte production, and to prolong neutrophil survival. The 127 amino acid sequence of natural human GM-CSF is presented herein as SEQ. ID. No. 3. The amino acid sequence of murine (Sparrow, L. et al., (1985) Proc. Natl. Acad. Sci. USA 82:292–296) and gibbon GM-CSF (Burgess, A. W., et al., (1986) Biochem. J. 235:805–814) have also been described. The primary amino acid sequences of GM-CSF strongly predict two $\alpha$-helices close to the N-terminus (positions 13 to 27 and 31 to 46 in the murine molecule), which appear to be required for biological activity. Truncation of either helix by introduction of a helix breaking glycine residue markedly reduced the activity of the molecule (Gough, N. M. (1987) Eur. J. Biochem. 169:353–358 (1987). Functional variants or analogs of human GM-CSF that comprise at least one substitution, deletion or insertion (e.g. Leu23, Asp27, Glu39), which inactivates an N-glycosylation site, thereby facilitating microbial expression are described in U.S. Pat. Nos. 5,032,676 and 5,229,496. Pharmacokinetic studies of GM-CSF by enzyme-linked immunoabsorbent assay and bioassay show that for intravenous and subcutaneous routes, serum concentrations are related to dose, though this relation is not strictly linear (Cebon, J. et al., (1988) Blood 72:1340–47). After intravenous administration over 30 min there is a distribution half-life (T sub ½ alpha) of 5–15 min and an elimination phase (T sub ½ Beta) of 1–9 h. After single subcutaneous bolus injections, peak serum concentrations are reached within 4 h and the elimination half-life is 2.9 h at doses of 10 m$\mu$ g/kg. At subcutaneous doses of 5–10 m$\mu$ g/kg serum concentrations >=10 ng/mL are achieved for 8–24 h.

"Infection" denotes invasion by a microorganism, such as a bacteria (e.g.

Enterobacteriaceae sp., Enterococcus sp., Haemophilus influenza, Mycobacterium tuberculosis, Neisseria gonorrhoeae, Plasmodiumfalciparum, Pseudomonas aeruginosa, Shigella dysenteriae, Staphylococcus aureus, Streptococcus pneumoniae), virus (e.g. HIV, herpes, hepatitis), fungi (e.g. Candida sp.), or protozoa.

"Inflammation" refers to locations of tissue damage in an individual, regardless of the underlying cause or etiology. For example, the tissue damage can result from microbial invasion (an infection), autoimmune processes, tissue or organ allograft rejection, neoplasia, idiopathic diseases or such injurious external influences as heat, cold, radiant energy, electrical or chemical stimuli, or mechanical trauma. Whatever the cause, the ensuing inflammatory response is quite similar consisting of a complicated set of functional and cellular adjustments involving changes in microcirculation, movement of fluids, and influx and activation of inflammatory cells (e.g. leukocytes).

A "label" refers to molecule that is capable of generating a detectable image that can be detected either by the naked eye or using an appropriate instrument, e.g. positron emission tomography (PET), single photon emission tomography (SPECT) or magnetic resonance imaging (MRI). Certain preferred labels are radionuclides. Particularly preferred radionuclides are selected from the group consisting of $^{123}$I, $^{99m}$Tc, $^{18}$F, $^{68}$Ga, $^{62}$Cu, $^{111}$In. Additional labels are suitable for obtaining a magnetic resonance image (MRI), including unpair spin atoms and free radicals (e.g. iron, lanthides and gadolinium) and contrast agents (e.g. chelated DTPA manganese).

"Peptides" refers to polymerized amino acids with a relatively small number of residues (i.e. in the range of about 2 to about 50) and a defined sequence.

A "pharmaceutically acceptable carrier" refers to a biocompatible solution, having due regard to sterility, pH, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

"Polypeptide" refers to polymerized amino acids comprised of a larger number of residues than a peptide (i.e. greater than about 50 amino acids)

"Protein" refers to a polypeptide that occurs naturally and has a definite three dimensional structure under physiological conditions.

"Subject" shall mean a human or animal (e.g. a non-human mammal (e.g. rat, mouse, cat, dog, horse, sheep, cow, monkey, avian, or amphibian)

A "therapeutic agent" refers to an agent that is capable of producing a biological effect in a subject. Preferred therapeutic agents are capable of preventing the establishment of or treating a site of infection or inflammation. Examples include antimicrobial agents including: aminoglycosides, amphenicols, β-lactams (e.g. carbapenems, cephalosporins, cephamycins, monobactams, oxacephems and penicillins), lincosamides, macrolides, polypeptides and peptides (e.g. defensins, bacitracin, polymyxin, cecropins, magainin II, indolicidin, ranalexin, protegrins, gallinacins, tritrpticin, lactoferricin, drosomycin, holotricin, thanatin, dermaseptin, iturins, syringomycins, nikkomycins, polyoxins, FR-900403, echinocandins, pneumocandins, aculeacins, mulundocandins, WF11899, aureobasidins, schizotrin A, cepacidines, zeamatin, cyclopeptides and D4e1), tetracyclines, 2,4-diaminopyrimidines, nitrofurans, quinolones and analogs, sulfones, sulfonamides; antifungal agents including: polyenes, allyamines, imidazoles, triazoles; antivirals including: purines/pyrimidinones (e.g. acyclovir, dideoxy-cytidine, -adenosine, or -inosine, interferons, amantadine, ribavirin); radionuclides (e.g. $^{131}$I, $^{186}$Re, $^{188}$Re, $^{90}$Y, $^{212}$Bi, $^{211}$At, $^{89}$Sr, $^{166}$Ho, $^{153}$Sm, $^{67}$Cu and $^{64}$Cu; and antiinflammatory agents including non-steroidal agents, such as aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives thiazinecarboxamides and others, as well as steroidal agents, such as glucocorticoids. For other antimicrobial and antiinflammatory agents, see e.g. the Merck Index. In addition to therapeutic agents that are currently in use, the instant invention contemplates agents that are in development or will be developed and that are useful for treating or preventing the progression of an infection or inflammatory response, e.g., antisense therapies.

General

The invention is based, at least in part, on the surprising finding that radiolabeled G-CSF effectively localizes to sites of infection. This empirical result is surprising, since the expression level of CSF receptors on cells has been found to be relatively low, compared to the expression level of other growth factor receptors on hematopoietic cells (Park et al., "Hemopoietic Growth-Factor Receptors" p39–75 in). Based on the cross-reactivity between CSFs and CSF receptors (Walker, F., and A. W. Burgess (1987) *J. Cell. Physiol.* 130:255–261), it is expected that other CSFs will also bind to sites of infection.

Based on the instant disclosed specificity of G-CSF to localize at sites of infection and inflammation, the invention features novel agents that target sites of infection and inflammation in vivo and methods for using the agents to identify, prevent and/or treat sites of infection and inflammation.

Method for Making Agents that Target Sites of Infection and Inflammation

In accordance with the invention, a CSF is associated with (brought into spatial proximity to) a label or therapeutic agent. Spatial proximity between the CSF and label or therapeutic agent may be effected in any manner which preserves the binding specificity of the CSF for a site of infection or inflammation. For example, spatial proximity may be effected by a covalent or non-covalent chemical bond. Such a chemical bond may occur directly or through a chemical intermediary, e.g. a chelator whereby the chelator is conjugated to the CSF prior to or after insertion of radiolabel in the chelator. For example, the label or therapeutic agent can be directly conjugated to a CSF via: 1) any free amino group (ε-amino groups at lysine residues or a free amine group at the N-terminus of a CSF) 2) a free sulfhydryl group (e.g. on a cysteine residue that is already present or engineered into the CSF), or 3) a carbohydrate moiety. Chelating agents, which are particularly useful for conjugating radioisotopes to CSFs, include: diethylene triamine pentaacetic acid (DTPA) (Hnatowich, D. J., (1982) *Int. J. Appl. Radiat. Isot.* 33:327–332) and ethylene diamine tetraacetic acid (EDTA). Examples of other chelating groups include dioxime ligands, functionalized cyclams, $N_2S_2$ ligands, $N_3S$ ligands, an isonitrile, a hydrazine, a HYNIC (hydrazinonicotinic acid), a 2-methylthiolnicotinic acid, or a carboxylate. In addition, a reactive thiol can be attached to a lysine residue via iminothiolane or thiol residues can be conjugated to a CSF using an amino sequence containing one or more cysteine residues.

Alternatively, association between a label or therapeutic agent and a CSF can be effected via an auxiliary molecule such as mannitol, gluconate, glucoheptonate, tartrate, and the like or by incorporating the label or therapeutic agent and the CSF into a micelle, microsphere or liposome. Preferably, the chelating structure, auxiliary molecule, or label is placed in spatial proximity to any position of the CSF which does not interfere with the interaction of the CSF with the target site of infection or inflammation.

Labels may be placed in spatial proximity to a CSF using known procedures which are specific to the label. For example, when using $^{123}$I, the CSF may be labeled in accordance with the known radioiodination procedures such as direct radioiodination with chloramine T, iodogen, lactoperoxidase, or indirectly via radioiodination exchange for a halogen or an organometallic group of a pendant moiety subsequently attached to CSF. When the radionuclide is $^{99m}$Tc, the imaging agent may be labeled using any method suitable for attaching $^{99m}$Tc to the CSF. Preferably, when the radionuclide is $^{99m}$Tc, an auxiliary molecule such as mannitol, gluconate, glucoheptonate, or tartrate is included in the labeling reaction mixture, with or without a chelating structure. More preferably, $^{99m}$Tc is placed in spatial proximity to the targeting molecule by reducing $^{99m}$TcO$_4$ with tin in the presence of mannitol and the targeting molecule. Other reducing agents, including tin tartrate or non-tin reductants such as sodium dithionite. Disulfide reduction an technetium insertion according to the Schwarz method may also be used.

After the labeling reaction is complete, the reaction mixture may optionally be purified using one or more chromatography steps such as Sep Pack or high performance liquid chromatography (HPLC). Any suitable HPLC system may be used if a purification step is performed, and the yield of agent obtained from the HPLC step may be optimized by varying the parameters of the HPLC system, as is known in the art. Any HPLC parameter may be varied to optimize the yield. For example, the pH may be varied, e.g., raised to decrease the elution time of the peak corresponding to the targeting agent of the invention.

Agents comprising a CSF and label or therapeutic agent can be tested for ability to bind a site of infection or inflammation as described in the following examples. Alternatively, the agents can be tested for binding in in vitro assays in cells or cell lines of the myelomonocytic lineage.

Kits

The invention as embodied in a kit for imaging or therapy comprises one or more of the compositions described above, in combination with a pharmaceutically acceptable carrier such as human serum albumin. Human serum albumin for use in the kit of the invention may be made in any way, for example, through purification of the protein from human serum or though recombinant expression of a vector containing a gene encoding human serum albumin. Other substances may also be used as carriers in accordance with this embodiment of the invention, for example, detergents, dilute alcohols, carbohydrates, auxiliary molecules, and the like. The kit of the invention may of course also contain such other items as may facilitate its use, such as syringes, instructions, buffers, reducing agents, buffers, reducing agents, reaction vials, and the like.

In one embodiment, a kit according to the invention contains from about 1 to about 30 mCi of the radionuclide-labeled imaging agent described above, in combination with a pharmaceutically acceptable carrier. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

In another embodiment, the kit of the invention may contain the targeting molecule which has been covalently or non-covalently combined with a chelating agent; an auxiliary molecule such as mannitol, gluconate, glucoheptonate, tartrate, and the like; and a reducing agent such as $SnCl_2$, Na dithionite or tin tartrate. The targeting molecule/chelating agent and the auxiliary molecule may be present as separate components of the kit or they may be combined into one kit component. The unlabeled targeting molecule/chelating agent, the auxiliary molecule, and the reducing agent may be provided in solution or in lyophilized form, and these components of the kit of the invention may optionally contain stabilizers such as NaCl, silicate, phosphate buffers, ascorbic acid, gentisic acid, and the like. Additional stabilization of kit components may be provided in this embodiment, for example, by providing the reducing agent in an oxidation-resistant form.

Determination and optimization of such stabilizers and stabilization methods are well within the level of skill in the art. When the targeting molecule/chelating agent of this embodiment are in lyophilized form, the kit may optionally contain a sterile and physiologically acceptable reconstitution medium such as water, saline, buffered saline, and the like. The amounts of unlabeled targeting molecule/chelating agent, auxiliary molecule, and reducing agent in this embodiment are optimized in accordance with the methods for making the cardiovascular imaging agent set forth above. Radionuclides, including, but not limited to, $^{99m}Tc$ obtained from a commercially available $^{99}Mo/^{99m}Tc$ generator or commercially available 123I, may be combined with the unlabeled targeting molecule/chelating agent and the reducing agent for a time and at a temperature sufficient to chelate the radionuclide to the targeting molecule/chelating agent, and the imaging agent thus formed is injected into the patient.

Use of Therapeutic Agents

For use in treating or preventing the development of an infection or inflammation, a therapeutically effective amount of therapeutic agent of the invention alone or in conjunction with a "pharmaceutically acceptable carrier" can be administered to a subject by any mode that allows the agent to be delivered to the infection or inflammation site. Preferred routes of administration include administration via injection (subcutaneous, intravenous, parenteral, intraperitoneal, intrathecal, etc.). The injection can be in a bolus or a continuous infusion. Depending on the route of administration, the therapeutic agent can be coated with or disposed within a selected material (e.g. positively or negatively charged liposomes), to protect the agent from natural conditions, which may detrimentally effect its ability to perform its intended function, increase its in vivo availability or increase its localization at sites of infection and inflammation.

A "therapeutically effective amount" of a therapeutic agent refers to that amount necessary or sufficient to eliminate, reduce or contain (prevent the spread of) an infection or inflammation. The "therapeutically effective amount" can vary depending on such factors as the infection or inflammation being treated, the particular therapeutic agent, the size of the subject, or the severity of the infection or inflammation. However, one of ordinary skill in the art can empirically determine the effective amount of a particular compound without performing undue experimentation.

Use of Imaging Agents

Imaging agents of the invention may be used in accordance with the methods of the invention by one of skill in the art, e.g., by specialists in nuclear medicine, to image sites of infection or inflammation in a subject. Any site of infection or inflammation may be imaged using the imaging agents of the invention.

Images can be generated by virtue of differences in the spatial distribution of the imaging agents which accumulate at a site of infection or inflammation. The spatial distribution may be measured using any means suitable for the particular label, for example, a gamma camera, a PET apparatus, a SPECT apparatus, and the like. Some lesions may be evident when a less intense spot appears within the image, indicating the presence of tissue in which a lower concentration of imaging agent accumulates relative to the concentration of imaging agent which accumulates in surrounding tissue. Alternatively, a lesion may be detectable as a more intense spot within the image, indicating a region of enhanced concentration of the imaging agent at the site of the lesion relative to the concentration of agent which accumulates in surrounding tissue. Accumulation of lower or higher amounts of the imaging agent at a lesion may readily be detected visually. Alternatively, the extent of accumulation of the imaging agent may be quantified using known methods for quantifying radioactive emissions. A particularly useful imaging approach employs more than one imaging agent to perform simultaneous studies.

Preferably, a detectably effective amount of the imaging agent of the invention is administered to a subject. In accordance with the invention, "a detectably effective amount" of the imaging agent of the invention is defined as an amount sufficient to yield an acceptable image using equipment which is available for clinical use. A detectably effective amount of the imaging agent of the invention may be administered in more than one injection. The detectably effective amount of the imaging agent of the invention can vary according to factors such as the degree of susceptibility of the individual, the age, sex, and weight of the individual, idiosyncratic responses of the individual, the dosimetry. Detectably effective amounts of the imaging agent of the invention can also vary according to instrument and film-related factors. Optimization of such factors is well within the level of skill in the art.

The amount of imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician will decide the amount of imaging agent to administer to each individual patient and the duration of the imaging study.

The present invention is further illustrated by the following examples which should not be construed as limiting in any way. The contents of all cited references (including literature references, issued patents, published patent applications) as cited throughout this application are hereby expressly incorporated by reference. The practice of the present invention will employ, unless otherwise indicated, conventional techniques, which are within the skill of the art. Such techniques are explained fully in the literature.

EXAMPLE 1

$^{111}$In-DTPA-GCSF

In order to label G-CSF with radioindium ($^{111}$In), G-CSF was conjugated with diethylenetriaminepentacetic acid (DTPA) via the active ester. DTPA conjugated G-CSF was labeled with In-111 and injected into rabbits bearing intramuscular bacterial infections. Two New Zealand white rabbits weighing approximately 2–3 kg were injected in their left posterior thigh with a 0.5 ml suspension of ~$10^9$ E. coli for infection imaging and biodistribution studies. Animals were injected with In-111-DTPA-G-CSF at 24 hr after bacterial injection, when the animals were judged to have moderate infections by palpation.

At 4 and 18 hours following injection of the In-111-DTPA-G-CSF, the animals were anesthetized with ketamine/xylazine (15.0 and 1.5 mg/kg) and scintigrams were acquired using a large field of view gamma camera equipped with a parallel hole medium energy collimator. Regions-of-interest (ROI's) were drawn over the area of infection and the contralateral normal muscle and target-to-background (T/B) ratios were calculated. After acquiring the final images, the animals were sacrificed with an over dose of sodium pentobarbital and biodistribution was determined. For comparison with the imaging results, infected to normal muscle and pus to normal muscle ratios were calculated from biodistribution data.

From ROI analysis, the average Target:Background (T/B) ratios were 3.567:1 and 11.87:1 at 4 and 18 hours post injection, respectively.

TABLE 1

T/B ratios calculated from ROI analysis of scintigrams at various times after injection.

|  | 3 hour | 6 hours | 17 hours |
|---|---|---|---|
| $^{99m}$Tc-fMLF | 3.63 ± 0.37, | 5.66 ± 1.97 | 10.47 ± 2.78 |
| $^{111}$In-WBC's | 2.41 ± 1.15, | 1.76 ± 0.23 | 5.45 ± 2.37 |
| $^{111}$In-DTPA-G-CSF | 3.567 | n.d. | 11.87 |

The results of this study, as shown in Table 1, indicate that In-111-DTPA-G-CSF is an effective agent for localizing sites of infection.

The following biodistribution data suggests that a significant mechanism for infection localization is via in vivo binding to WBC'S.

TABLE 2

Biodistribution data (% injected dose/g) in Rabbits of In-111-DTPA-GCSF at 18 hours post injection.

| Organ: | Rabbit #1 | Rabbit #2 | Average |
|---|---|---|---|
| Blood | 0.0077 | 0.00789 | 0.00782 |
| Heart | 0.00644 | 0.00787 | 0.00715 |
| Lung | 0.0702 | 0.1375 | 0.1038 |
| Liver | 0.0394 | 0.0506 | 0.04498 |
| Spleen | 0.07346 | 0.18946 | 0.1315 |
| Kidney | 1.132 | 1.3497 | 1.2411 |
| Adrenal | 0.0247 | 0.0209 | 0.0228 |
| Stomach | 0.01198 | 0.00866 | .01032 |
| GI tract | 0.0142 | 0.0159 | 0.0151 |
| Testes | 0.0046 | 0.0075 | 0.0061 |
| Skeletal Muscle | 0.0015 | 0.002 | 0.00175 |
| Infected muscle #1 | 0.0555 | 0.07797 | 0.0667 |
| Infected muscle #2 | 0.0324 | 0.052 | 0.0422 |
| Infected muscle #3 | 0.0303 | 0.0736 | 0.051 |
| Infected muscle #4 | 0.032 | 0.0565 | 0.044 |
| Infected muscle #5 | 0.0235 | 0.0326 | 0.0281 |
| Pus | 0.035 | 0.1884 | 0.112 |
| Marrow | 0.0386 | 0.068 | 0.053 |
| Bone | 0.0031 | 0.0351 | 0.0191 |

TABLE 3

Infected to Normal Tissue Ratios in Rabbits Injected With In-111-DTPA-GCSF at 18 Hours Post Injection.

| Tissue | Rabbit #1 | Rabbit #2 | Average |
|---|---|---|---|
| Infected/normal muscle #1 | 36.89 | 39.21 |  |
| Infected/normal muscle #2 | 21.54 | 26.17 |  |
| Infected/normal muscle #3 | 20.11 | 37.03 |  |
| Infected/normal muscle #4 | 20.95 | 28.44 |  |
| Infected/normal muscle #5 | 15.63 | 16.42 |  |
| Infected/normal muscle | — | — | 26.24 |
| Pus/normal muscle | 23.56 | 94.76 | 59.16 |

TABLE 4

Infected to normal tissue ratios calculated from gamma camera images in Rabbits of In-111-DTPA-GCSF at 4 and 18 hours post injection.

|  | 4 hours | 18 hours |
|---|---|---|
| Rabbit #1 | 3.359 | 8.643 |
| Rabbit #2 | 3.775 | 15.10 |
| Average | 3.567 | 11.87 |

EXAMPLE 2

$^{99m}$Tc-BIO-100

Tc-99m-labeled-BIO-100 was injected into rabbits bearing intramuscular bacterial infections. New Zealand white rabbits weighing approximately 2.5 kg were injected in their left posterior thigh with a 0.5 ml suspension of ~10$^9$ *E. coli* for infection imaging and biodistribution studies. Animals were injected with Tc-99m-BIO-100 at 24 hr after bacterial injection, when the animals were judged to have moderate infections by palpation.

At 18 hours following injection of the Tc-99m-BIO-100, the animals were anesthetized with ketamine/xylazine (15.0 and 1.5 mg/kg) and scintigrams were acquired using a large field of view gamma camera equipped with a parallel hole medium energy collimator. After acquiring the final images, the animals were sacrificed with an over dose of sodium pentobarbital and biodistribution was determined. For the comparison with the imaging results, infected to normal muscle and pus to normal muscle ratios were calculated from the biodistribution data.

From ROI analysis, the average Target:Background (T/B) ratios were 1.999:1 and 7.024:1 at 3 and 18 hours post injection, respectively.

TABLE 5

Biodistribution data (% injected dose/g) in Rabbits of Tc-99m-BIO-100 at 18 hours post injection

| Organ: | Rabbit #1 | Rabbit #2 | Average |
|---|---|---|---|
| Blood | 0.06047 | 0.05468 | 0.05758 |
| Heart | 0.03214 | 0.03251 | 0.03233 |
| Lung | 0.10415 | 0.17054 | 0.13735 |
| Liver | 0.11087 | 0.09261 | 0.10174 |
| Spleen | 0.20240 | 0.24238 | 0.22239 |
| Kidney | 1.29451 | 1.57905 | 1.43678 |
| Adrenal | 0.07034 | 0.04626 | 0.05830 |
| Stomach | 0.02528 | 0.02629 | 0.02578 |
| GI Tract | 0.03378 | 0.03419 | 0.03398 |
| Testes | 0.04274 | 0.02508 | 0.03391 |
| Skeletal Muscle | 0.00430 | 0.00333 | 0.00382 |
| Infected muscle #1 | 0.09042 | 0.10711 | 0.09877 |
| Infected muscle #2 | 0.13403 | 0.13028 | 0.13216 |
| Infected muscle #3 | 0.11394 | 0.10416 | 0.10905 |
| Infected muscle #4 | 0.08262 | 0.09098 | 0.08680 |
| Infected muscle #5 | 0.08147 | 0.07411 | 0.07779 |
| Pus | 0.05763 | 0.17865 | 0.11814 |
| Marrow | 0.17399 | 0.10780 | 0.14089 |
| Bone | 0.03533 | 0.02188 | 0.02860 |

TABLE 6

Infected to Normal Tissue Ratios in Rabbits Injected With Tc-99m-BIO-100 at 18 Hours Post Injection.

| Tissue | Rabbit #1 | Rabbit #2 | Average |
|---|---|---|---|
| Infected/normal muscle #1 | 21.01 | 32.13 | |
| Infected/normal muscle #2 | 31.15 | 39.07 | |
| Infected/normal muscle #3 | 26.47 | 31.24 | |
| Infected/normal muscle #4 | 19.20 | 27.29 | |
| Infected/normal muscle #5 | 18.93 | 22.23 | |
| Infected/normal muscle | — | — | 26.87 |
| Pus/normal muscle | 13.39 | 53.58 | 33.48 |

TABLE 7

Infected to normal tissue ratios calculated from gamma camera images in Rabbits of Tc-99m-BIO-100 at 3 and 18 hours post injection.

| | 3 hours | 18 hours |
|---|---|---|
| Rabbit #1 | 2.554 | 10.67 |
| Rabbit #2 | 1.444 | 3.377 |
| Average | 1.999 | 7.024 |

What is claimed is:

1. A method of detecting a site of infection or inflammation in a subject comprising the steps of:
   a) administering to the subject a diagnostically effective amount of an imaging agent comprising a colony stimulating actor (CSF) and a label, and
   b) detecting a sufficient amount of the label as an indication of a site of infection or inflammation.

2. The method of claim 1, wherein the imaging agent is administered intaveneously, subcutaneously, parenterally, intraperitoneally, or intrathecally.

3. The method of claim 1, wherein the CSF is selected from the group consisting of: granulocyte colony-stimulating factor (G-CSF), granulocyte-macrophage colony-stimulating factor (GM-CSF), monocyte colony stimulating factor (M-CSF or CSF-1) and binding fragments thereof.

4. The method of claim 1, wherein the CSF is recombinant.

5. The method of claim 1, wherein the CSF is wildtype.

6. The method of claim 1, wherein the CSF is fully glycosylated.

7. The method of claim 1, wherein the CSF is a full-length protein.

8. The method of claim 1, wherein the CSF is a polypeptide.

9. The method of claim 1, wherein the CSF is a peptide.

10. The method of claim 1, wherein the CSF is human.

11. The method of claim 1, wherein the agent exhibits a target to non-target ratio of at least about 5:1.

12. The method of claim 1, wherein the agent is stable in vivo.

13. The method of claim 1, wherein the agent substantially localizes to a site of infection or inflammation, whereby a lesion can be delineated, within about 18 hours after administration.

14. The method of claim 1, wherein the agent substantially localizes to a site of infection or inflammation within about 8 hours after administration.

15. The method of claim 1, wherein the label is a radionuclide.

16. The method of claim 1, wherein the radionuclide is selected from the group consisting of $^{123}$I, $^{99m}$Tc, $^{18}$F, $^{68}$Ga, $^{64}$Cu, $^{62}$Cu, $^{55}$Co and $^{111}$In.

17. The method of claim 16, wherein the radionuclide is $^{99m}$Tc.

18. The method of claim 16, wherein the radionuclide is $^{111}$In.

19. The method of claim 1, wherein the CSF is a component of a fusion protein.

20. The method of claim 1, wherein the infection is caused by a microorganism.

21. The method of claim 20, wherein the microorganism is a bacteria, virus, fungi, or protozoa.

22. The method of claim 21, wherein the microorganism is selected from the group consisting of *Escherichia Coli*, Enterobacteriaceae sp., Enterococcus sp., *Haemophilus influenza, Mycobacterium tuberculosis, Neisseria gonorrhoeae, Plasmodium falciparum, Pseudomonas aeruginosa, Shigella dysenteriae, Staphylococcus aureus, Streptococcus pneumonia,* HIV, herpes, hepatitis, and Candida sp.

23. The method of claim 1, wherein the site of inflarmmation is caused by a microbial invasion, autoimmune process, tissue or organ allograft rejection, neoplasia, idiopathic disease, or mechanical trauma.

24. The method of claim 1, wherein the label is detected by a gamma camera. positron emission tomography (PET), single photon emission tomography (SPECT), or magnetic resonance imaging (MRI).

25. The method of claim 1, wherein the subject is a human, rat, mouse, cat, dog, horse, sheep, cow, monkey, avian, or amphibian.

26. The method of claim 1, wherein the label is conjugated to CSF via a chelating agent.

27. The method of claim 26, wherein the chelating agent is selected from the group consisting of diethylene trianine pentaacetic acid (DTPA), ethylene diarine tetraacetic acid (EDTA), dioxirne ligand, functionalized cyclam, $N_2S_2$ ligand, $N_3S$ ligand, isonitrile, hydrazine, HYNIC (hydrazinonicotinic acid), 2-methylithiolnicotinic acid, and a carboxylate.

* * * * *

UNITED STATES PATENT AND TRADEMARK OFFICE
CERTIFICATE OF CORRECTION

PATENT NO.    : 6,491,893 B1
DATED         : December 10, 2002
INVENTOR(S)   : John W. Babich It is certified that error appears in the above-identified patent and that said Letters Patent is hereby corrected as shown below:

<u>Title page, Item [54] and Column 1, line 1,</u>
Title of Invention, please insert the word -- NOVEL -- before the word "COMPOUNDS"
Item [63], Related U.S. Application Data, please replace "PCT/US00/01289 filed on January 19, 2001" with -- PCT/US00/01289 filed on January 19, 2000 --

Signed and Sealed this

Ninth Day of September, 2003

JAMES E. ROGAN
*Director of the United States Patent and Trademark Office*